(12) United States Patent
Mulpuru

(10) Patent No.: US 10,517,537 B2
(45) Date of Patent: Dec. 31, 2019

(54) WEARABLE SYSTEM FOR MONITORING PHYSIOLOGICAL PARAMETERS OF A PERSON

(71) Applicant: Kesava Phani Krishna Mulpuru, Chennai (IN)

(72) Inventor: Kesava Phani Krishna Mulpuru, Chennai (IN)

(*) Notice: Subject to any disclaimer, the term of this patent is extended or adjusted under 35 U.S.C. 154(b) by 663 days.

(21) Appl. No.: 15/084,482

(22) Filed: Mar. 30, 2016

(65) Prior Publication Data

US 2017/0027513 A1  Feb. 2, 2017

(30) Foreign Application Priority Data

Jul. 30, 2015 (IN) .......................... 3911/CHE/2015
Dec. 1, 2015 (IN) .......................... 6462/CHE/2015

(51) Int. Cl.
| | |
|---|---|
| *A61B 5/00* | (2006.01) |
| *A61B 5/11* | (2006.01) |
| *A61B 5/01* | (2006.01) |
| *A61B 5/0205* | (2006.01) |
| *A61B 5/024* | (2006.01) |

(52) U.S. Cl.
CPC .......... *A61B 5/6831* (2013.01); *A61B 5/0002* (2013.01); *A61B 5/01* (2013.01); *A61B 5/1114* (2013.01); *A61B 5/1118* (2013.01); *A61B 5/681* (2013.01); *A61B 5/6833* (2013.01); *A61B 5/7246* (2013.01); *A61B 5/7282* (2013.01); *A61B 5/746* (2013.01); *A61B 5/02055* (2013.01); *A61B 5/02438* (2013.01)

(58) Field of Classification Search
CPC ..... A61B 5/0002; A61B 5/01; A61B 5/02055; A61B 5/02438; A61B 5/1114; A61B 5/1118; A61B 5/681; A61B 5/6831; A61B 5/6833; A61B 5/7246; A61B 5/7282; A61B 5/746
USPC .................................................. 600/300, 301
See application file for complete search history.

(56) References Cited

U.S. PATENT DOCUMENTS

| | | | |
|---|---|---|---|
| 2011/0224936 A1* | 9/2011 | Shimizu ................. | G01K 7/427 702/99 |
| 2015/0035680 A1* | 2/2015 | Li ........................... | G01K 1/14 340/584 |
| 2015/0182322 A1* | 7/2015 | Couse ..................... | G01K 1/20 600/549 |
| 2016/0038036 A1* | 2/2016 | Augustine .............. | G01K 1/165 600/549 |

(Continued)

*Primary Examiner* — Christopher Koharski
*Assistant Examiner* — James Moss

(57) ABSTRACT

A system is provided for monitoring physiological parameter(s) and providing a context under which the physiological parameter is measured. The system may include a data processing device. The data processing device may be configured to receive data corresponding to physiological parameter(s) measured from a body. The data processing device may be further configured to receive data that enables determination of one or more of orientation of the body and determination of movements of the body. The data processing device may be additionally configured to correlate and present the correlation between the measured physiological parameter(s) and one or more of orientation a body and activity the body is indulged in, which is derived based on the movements of the body.

6 Claims, 12 Drawing Sheets

(56) References Cited

U.S. PATENT DOCUMENTS

2016/0249174 A1\* 8/2016 Patel .................... G01K 13/002

\* cited by examiner

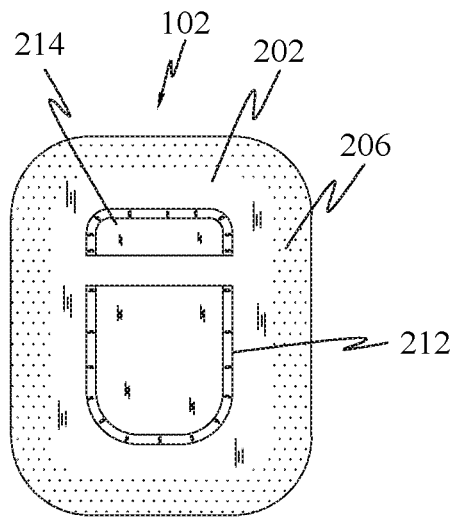
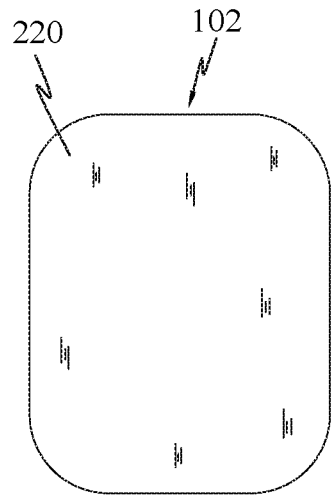
FIGURE 2A         FIGURE 2B
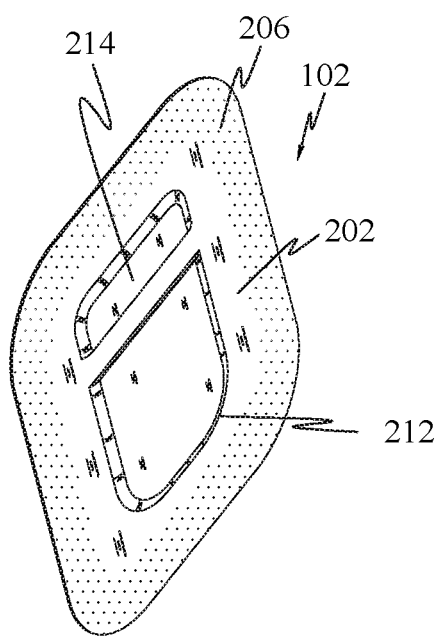
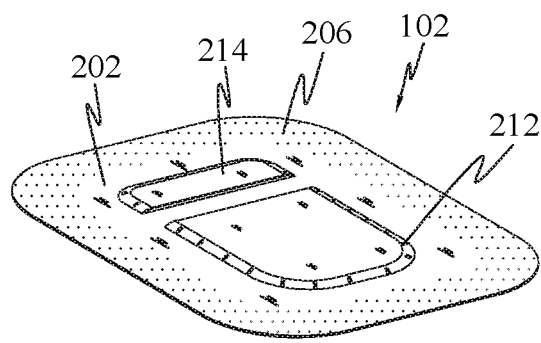
FIGURE 2C         FIGURE 2D

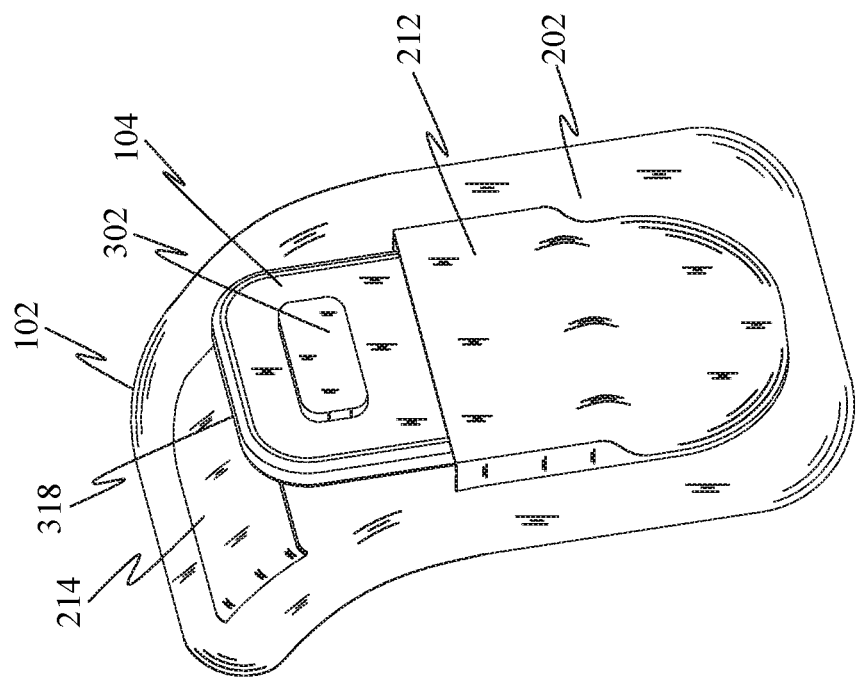
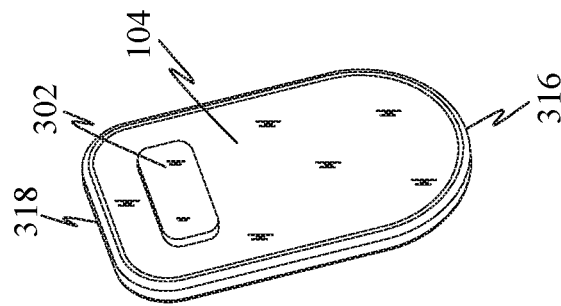
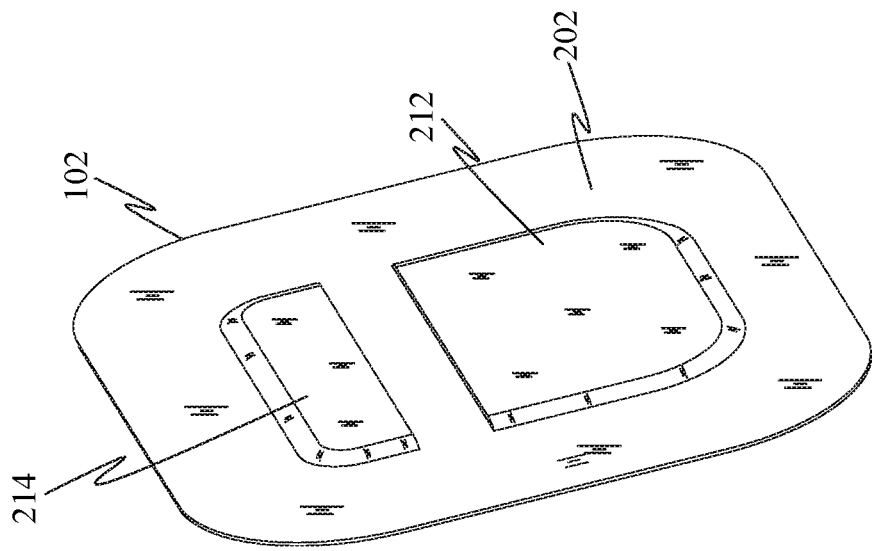
FIGURE 2E
FIGURE 2F

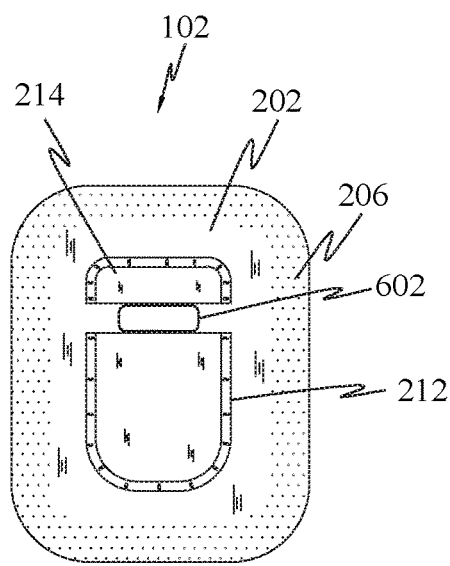
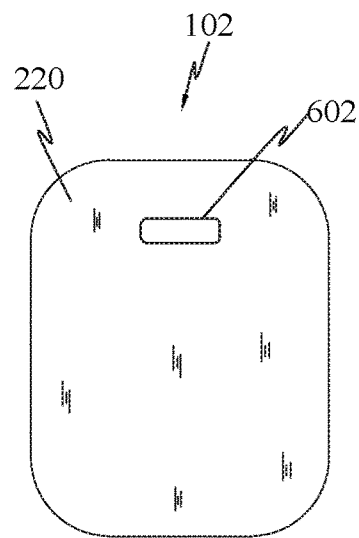
FIGURE 6A　　　　　　　　FIGURE 6B
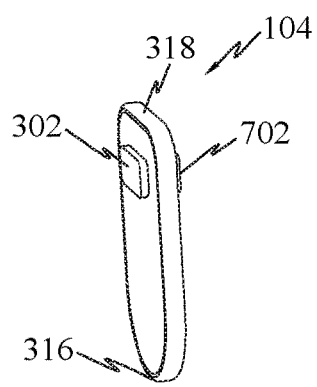
FIGURE 7

WEARABLE SYSTEM FOR MONITORING PHYSIOLOGICAL PARAMETERS OF A PERSON

CROSS REFERENCE TO RELATED APPLICATIONS

This application claims priority from Indian Application No. 3911/CHE/2015 filed on Jul. 30, 2015 and Indian Application No. 6462/CHE/2015 filed on Dec. 1, 2015 which is incorporated in its entirety herein by reference.

BACKGROUND

Technical Field

The present disclosure relates to medical device. More particularly, but not exclusively, the present disclosure relates to medical device for monitoring physiological parameters of a person and communicating the monitored physiological parameters.

Discussion of Related Art

Human body temperature is one of the vital parameters that may have to be monitored. Body temperature may be measured using electronic or non-electronic thermometers. A thermometer may be placed in the oral cavity or at the axilla to take measurements. Such conventional techniques require a care taker to take such measurements, especially when the measurements have to be taken on an infant. Another disadvantage of such conventional techniques is that continuous measurement of body temperature may not be practically feasible. Further, such techniques are intrusive in nature, and can be quite inconvenient if the measurement has to be taken while the person is asleep. Further, body temperature is conventionally measured when the person is asleep or when the person is ready for body temperature measurement by standing, sitting or any form that facilitates body temperature measurement. At times it is also important to measure body temperature when the person is carrying out day to day activities. However, the conventional technique may set a limitation whereby the person carrying out an activity has to stop his activity for having the temperature measurement taken. Further, conventional techniques fail to provide a context in which body temperature was measured.

In light of the foregoing discussion, there may be a need for a technique to enable continuous monitoring of body temperature and provide a context under which the body temperature was measured.

The background section is not intended to define the scope of the invention.

SUMMARY

In an embodiment a pouch configured to house a medical monitoring device is provided. The pouch may include a first side defining a cavity to receive the medical monitoring device. A portion of the medical monitoring device when received into the cavity is partially exposed out of the cavity. The first side is configured to be attached to a body. The pouch may further include a second side opposite to the first side. The second side faces away from the skin when the first side is attached to the body.

In an embodiment a medical monitoring device may be provided. The medical monitoring device may include a temperature sensor. The medical monitoring device may further include a housing configured to accommodate the temperature sensor. The housing comprises of a first member and a second member. The first member and the second member are assembled to form a housing by at least one among a interference fit and transition fit, thereby avoiding the need for an external fastener. The second member further defines an aperture configured to expose a portion of the temperature sensor.

An embodiment provides a system for monitoring physiological parameter(s) and providing a context under which the physiological parameter is measured. The system includes a data processing device. The data processing device may be configured to receive first data corresponding to physiological parameter(s) measured from a body. The data processing device may be further configured to receive second data that enables determination of one or more of orientation of the body and determination of movements of the body. The data processing device may be additionally configured to correlate and present the correlation between the measured physiological parameter(s) and one or more of orientation a body and activity the body is indulged in, which is derived based on the movements of the body.

In an embodiment a medical monitoring device may be provided. The medical monitoring device may include a first sensor and a second sensor. The first sensor is in physical contact with a body and is configured to measure a first temperature of the body at a first location on the body. The second sensor is configured to measure a second temperature. The second sensor is positioned such that the first sensor is in between the second sensor and the first location on the body.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 2A is a front view of a pouch 102 of the system 100 for monitoring physiological parameters of the person, in accordance with an embodiment.

FIG. 2B is a back view of the pouch 102 of FIG. 2A, in accordance with an embodiment.

FIG. 2C is an isometric view of the pouch 102 of FIG. 2A, in accordance with an embodiment.

FIG. 2D is another isometric view of the pouch 102 of FIG. 2A, in accordance with an embodiment.

FIG. 2E is an isometric view of a medical monitoring device 104 and the pouch 102 of the system 100 for monitoring physiological parameters of the person, in accordance with an embodiment.

FIG. 2F is an illustration depicting insertion of the medical monitoring device 104 into a first cavity 212 of the pouch 102, in accordance with an embodiment.

FIG. 6A is a front view of a pouch 102 of the system 100 for monitoring physiological parameters of a person, in accordance with an embodiment.

FIG. 6B is a back view of the pouch 102 of FIG. 6A, in accordance with an embodiment.

FIG. 7 is an isometric view of the medical monitoring device 104 with two temperature sensors for monitoring physiological parameters of a person, in accordance with an embodiment.

DETAILED DESCRIPTION

The disclosure relates to system and method for monitoring physiological parameters of a person and providing a context under which the physiological parameters are measured.

The following detailed description includes references to the accompanying drawings, which form a part of the detailed description. The drawings show illustrations in accordance with example embodiments. These example embodiments are described in enough detail to enable those skilled in the art to practice the present subject matter. However, it will be apparent to one of ordinary skill in the art that the present invention may be practiced without these specific details. In other instances, well-known methods, procedures, components, circuits, and networks have not been described in detail so as not to unnecessarily obscure aspects of the embodiments. The embodiments can be combined, other embodiments can be utilized, or structural, logical and electrical changes can be made without departing from the scope of what is claimed. The following detailed description is, therefore, not to be taken as a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Figure 1:
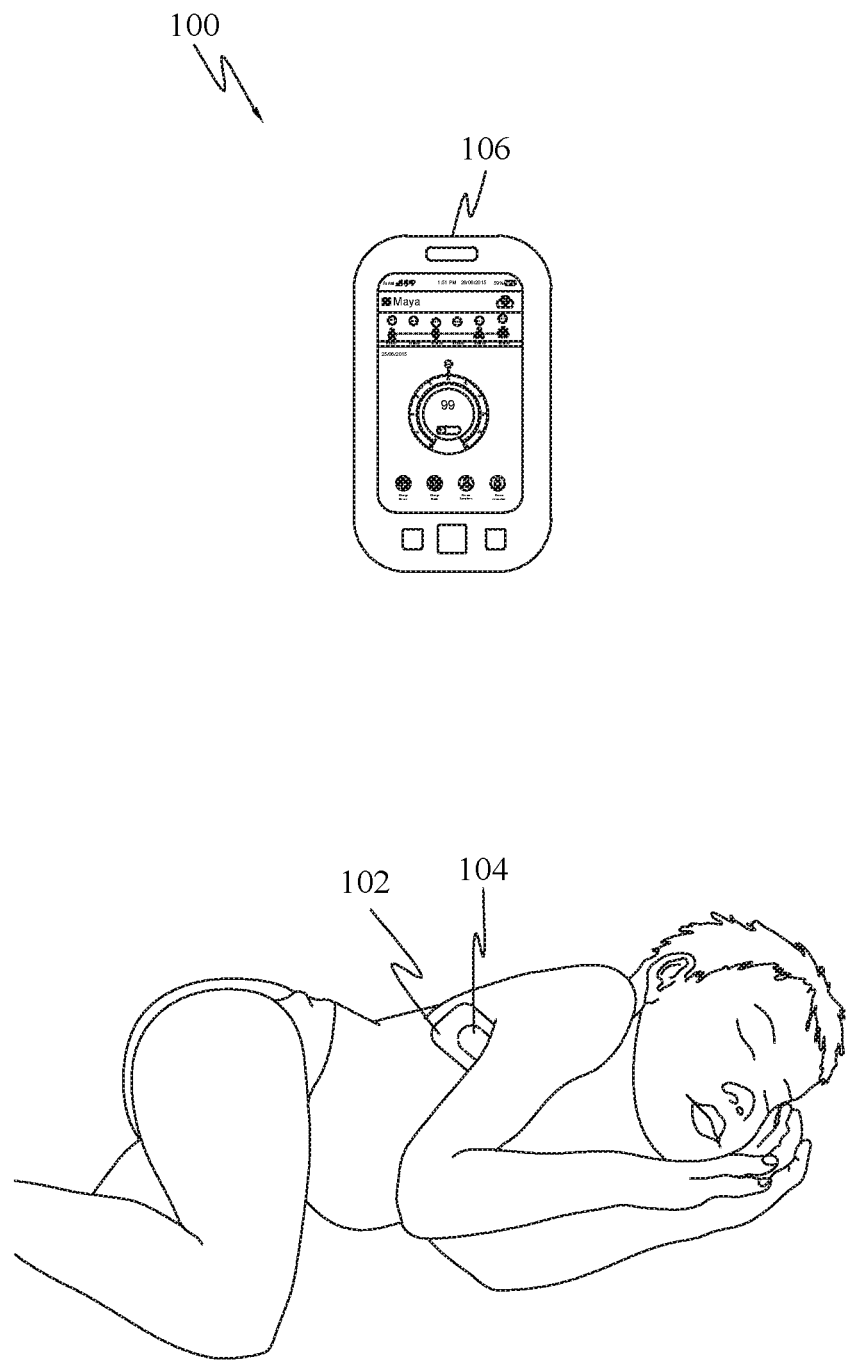
FIG. 1 is an illustration of an exemplary system 100 for monitoring physiological parameters of a person, in accordance with an embodiment.
Figure 2H:
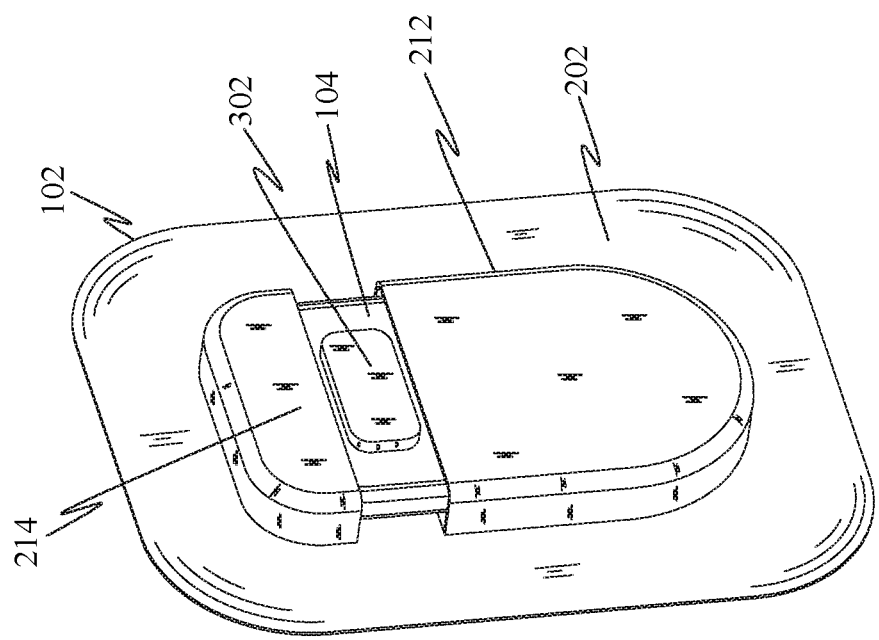
FIG. 2H is an illustration depicting the medical monitoring device 104 being held within the cavities 212, 214 of the pouch 102, in accordance with an embodiment.
Figure 2G:
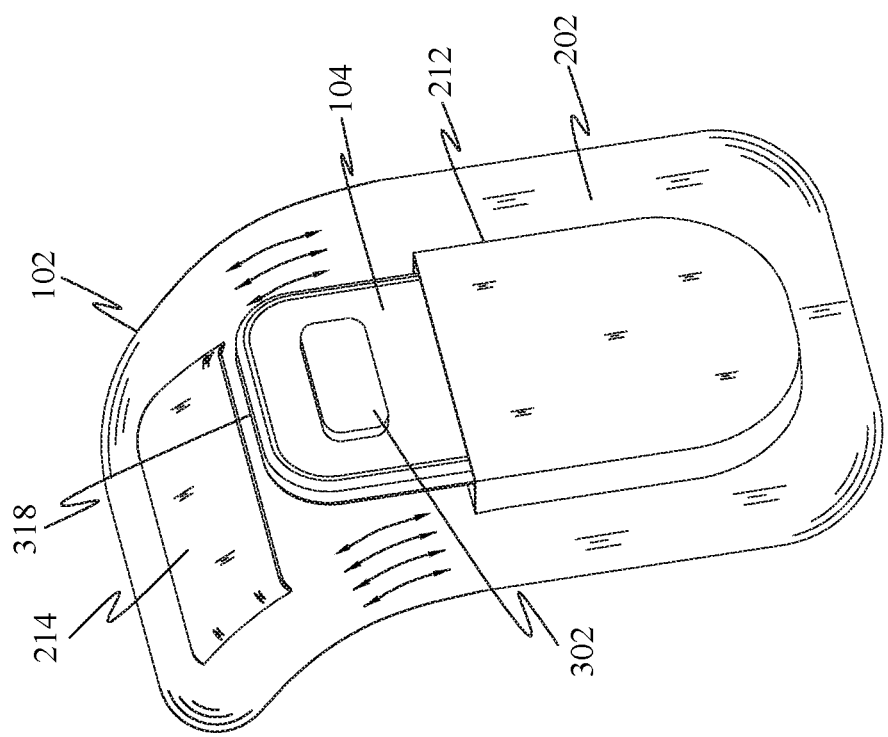
FIG. 2G is an illustration depicting insertion of the medical monitoring device 104 into a second cavity 214 subsequent to insertion into the first cavity 212 of the pouch 102, in accordance with an embodiment.

Referring to FIG. 1, a system 100 may be used for monitoring physiological parameters of a person and providing a context under which the physiological parameters are measured. The system 100 may include a pouch 102, a medical monitoring device 104 and a data processing device 106.

The medical monitoring device 104 may include a temperature sensor configured to measure body temperature of the person. The measured body temperature of the person may be referred to as first data. The medical monitoring device 104 may further include one or more sensors configured to collect second data that enables determination of orientation of the person. The one or more sensors may be further configured to collect second data that enables determination of movements (thereby the activities) of the person. An accelerometer is an example of such a sensor. The second data that enables determination of the orientation of the person and/or movements of the person may be referred to as body position data. The medical monitoring device 104 may further include a transmitter configured to transmit both the first data (a body temperature data) and the second data (the body position data) to a remote destination. Remote destination can mean and include data processing device(s) 106 in the vicinity of the medical monitoring device 104 or even a cloud based processing device in a central location.

The data processing device 106 may be configured to receive the body temperature data and the body position data that were transmitted by the transmitter, and correlate the body temperature with the position of the person to arrive at a result.

Referring to FIGS. 2A-2H, the pouch 102 is configured to house the medical monitoring device 104 and enable the medical monitoring device 104 to be engaged to a body (ex: human body). The pouch 102 may define a cavity which includes a first cavity 212 and a second cavity 214. The first cavity 212 and the second cavity 214 may be spaced apart, such that, when the medical monitoring device 104 is received within the first cavity 212 and the second cavity 214, a portion of the medical monitoring device 104 may be exposed out of the first cavity 212 and the second cavity 214, and may be capable of establishing direct contact with the skin.

The pouch 102 may be stretchable. A first portion 316 of the medical monitoring device 104 may be received into the first cavity 212. Subsequent to the first portion 316 being received into the first cavity 212 and upon stretching and releasing the pouch 102, a second portion 318 of the medical monitoring device 104 may be received into the second cavity 214. A portion of the first side 202 of the pouch 102 may include adhesive 206, thereby enabling the first side 202 of the pouch 102 to be attached to the external surface of the skin. The pouch 102 may include a second side 220 opposite to the first side, such that, the second side 220 will face away from the skin when the first side 202 is attached to the external surface of the skin.

In another embodiment, the pouch 102 may include only one cavity 212 instead of two cavities as described in the previous embodiment. A portion of the medical monitoring device 104 when received into a single cavity may be partially exposed out of the cavity. The medical monitoring device 104 may be received into the cavity when the medical monitoring device 104 is slid into the opening in a first direction. The medical monitoring device 104 may be removable from the cavity by sliding the medical monitoring device 104 in a second direction, wherein the second direction may be opposite to the first direction.

It may be noted the above described embodiments disclose a modular set-up. The modular set-up enables the medical monitoring device 104 to be used time and again, while disposing off the pouch 102 once used, or after a few uses. Hence, the expensive portion of the setup is retained for subsequent use, thereby reducing the cost involved in monitoring.

Figure 3A:
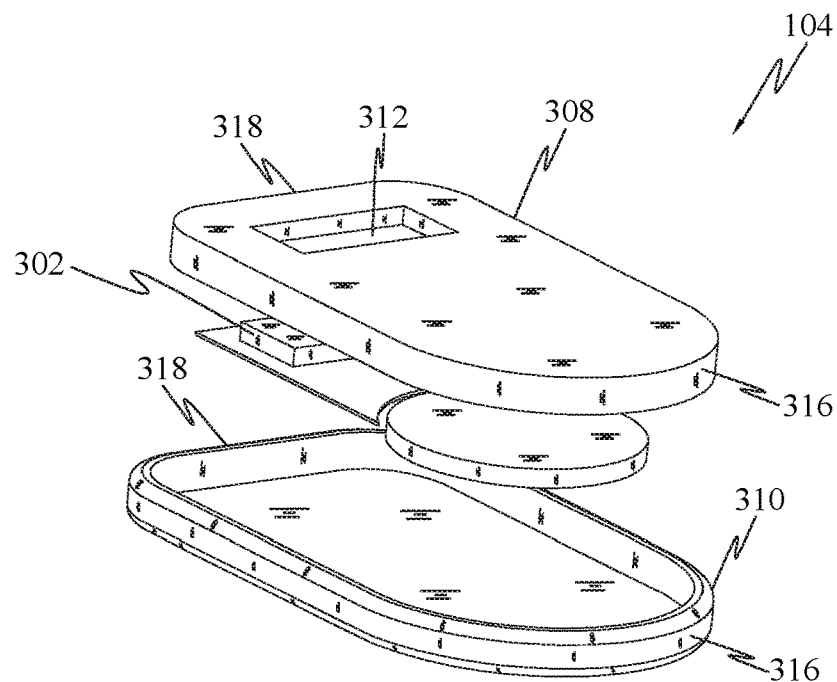
FIG. 3A is an exploded view of the medical monitoring device 104 of the system 100 for monitoring physiological parameters of the person, in accordance with an embodiment.
Figure 3B:
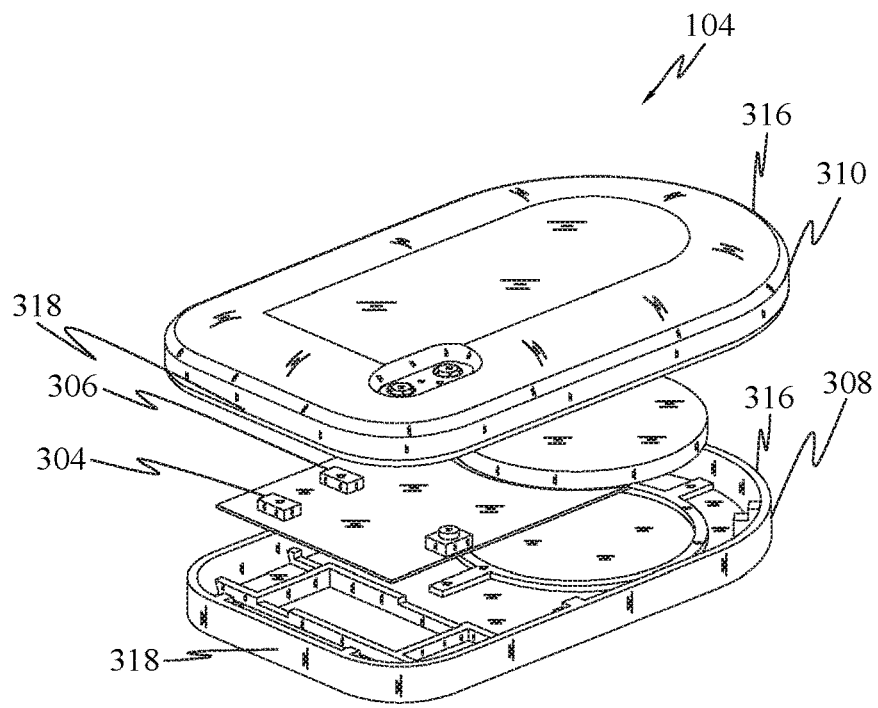
FIG. 3B is another exploded view of the medical monitoring device 104 of FIG. 3A, in accordance with an embodiment.

Referring to FIGS. 3A and 3B, the medical monitoring device 104 may include a housing. The housing may include a first member 308 and a second member 310. The housing may accommodate a battery, the temperature sensor 302, the position sensor 304 (one or more sensors configured to collect the second data that enables determination of one or more of orientation and movement), the transmitter 306, a processor and memory. The second member 310 may further define an aperture 312 configured to expose a portion of the temperature sensor 302. The first member 308 and the second member 310 may be assembled to form the housing by at least one among an interference fit and transition fit, thereby avoiding the need for an external fastener (example screw). This type of fit between the first member 308 and the second member 310 ensures that the medical monitoring device 104 is safer to use without any sharp protruding fasteners, easy to assemble and disassemble and replace battery. In an embodiment, one or more of the first member 308 and the second member 310 may be made of flexible material, such that it assumes the shape of the body to which the medical monitoring device 104 is attached.

FIG. 6A is a front view of a pouch 102 of the system 100 for monitoring physiological parameters of a person, in accordance with an embodiment. In the instant embodiment, the pouch 102 defines an aperture 602 to accommodate a second sensor 702 (as shown in FIG. 7) of the medical monitoring device 104. A back view of the pouch 102 with the aperture 602 is shown in FIG. 6B.

FIG. 7 is an isometric view of the medical monitoring device 104 with two temperature sensors for monitoring physiological parameters of a person, in accordance with an embodiment. In the instant embodiment the medical monitoring device 104 includes a temperature sensor 702 (also referred as second sensor) in addition to the temperature sensor 302 (also referred as first sensor).

The second sensor 702 may be configured to measure a second temperature which is the temperature of ambient air surrounding the second sensor 702.

The pouch 102 (as shown in FIGS. 6A and 6B) with the medical monitoring device 104 (as shown in FIG. 7) may be configured to secure the medical monitoring device 104 to the body of the person being monitored, such that, the first sensor 302 is in physical contact with the body. The first sensor 302 may be configured to measure a first temperature of the body at a first location on the body. As an example, the first location on the body may be a location under the arm of the body of the person being monitored. The second sensor 702 may be positioned, such that, the first sensor 302 is in between the second sensor 702 and the first location on the body. As an example, the second sensor 702 may be positioned to face axilla of a person being monitored. The second sensor 702 may be configured to measure the second temperature. In an embodiment, the second sensor 702 is in physical contact with the body at a second location to measure a second temperature. As an example, the second location on the body may be at axilla of the person being monitored.

In an embodiment, the processor of the medical monitoring device 104 may be configured to receive the first temperature from the first sensor 302 and the second temperature from the second sensor 702 to determine a core temperature of the body, which represents the actual or accurate temperature of the body core of the person being monitored.

In an embodiment, the processor of the medical monitoring device may be configured to receive the first temperature from the first sensor 302, the second temperature from the second sensor 702 and the body position data from the position sensor to determine a core temperature of the body, which represents the actual or accurate core temperature of the body of the person being monitored.

In an example, the core temperature of the body is determined using the following equation $$T_3 = F(T1, T2, P)$$

where, $T_1$=First temperature measured by the first sensor
$T_2$=Second temperature measured by the second sensor
P=The body position data
F(T1, T2, P)=Is a function of one or more of the first temperature, the second temperature and the body position data
$T_3$=Core temperature of the body In one embodiment, the medical monitoring device 104 is positioned such that the first sensor 302 is in contact with the body and the second sensor 702 faces the axilla of the person being monitored. Such positioning of the medical monitoring device 104 with respect to the body insulates the first sensor 302 and the second sensor 702 from ambient air. It may be understood that when the first sensor 302 and the second sensor 702 are insulated from ambient air, the core temperature of the body can be accurately determined.

In another embodiment, the medical monitoring device 104 is positioned such that at least one of the first sensor and the second sensor are not insulated from ambient air. The core temperature of the body may be determined by using the equation which may be a function of or more of the first temperature, the second temperature and the body position data.

In another embodiment, the transmitter 306 of the medical monitoring device 104 may be configured to transmit one or more of the first temperature, the second temperature (example: environmental data) and the body position data to the remote destination. Remote destination can mean and include data processing device(s) 106 in the vicinity of the medical monitoring device 104 or even a cloud based processing device in a central location.

The data processing device 106 or the cloud based processing device may be configured to determine the core temperature of the body and correlate it with the body position data (position of the person) to arrive at a result.

In another embodiment, the data processing device 106 may be configured to receive the body temperature data (first temperature), ambient temperature data (second temperature) and the body position data that were transmitted by the transmitter, and correlate the body temperature and the ambient temperature with the position of the person to arrive at a result.

In another embodiment, the data processing device 106 may be configured to receive the first temperature from the first sensor 302, the second temperature from the second sensor 702 and the body position data from the position sensor to determine the core temperature of the body, which represents the actual or accurate temperature of the body core of the person being monitored.

Figure 8A:
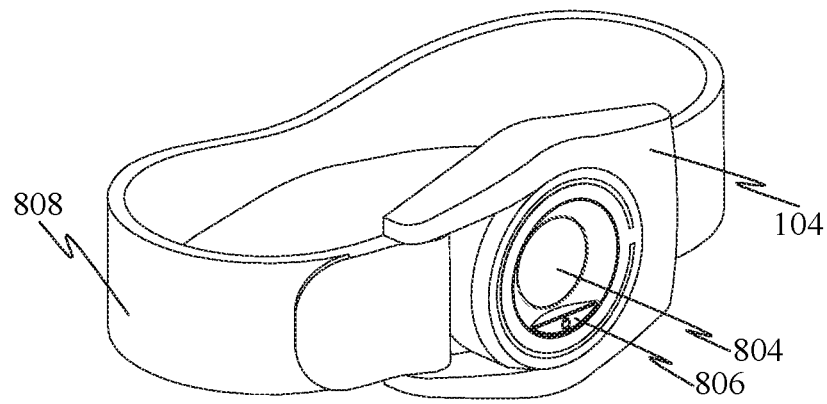
FIG. 8A is an isometric view of an armband configuration of the medical monitoring device 104 for monitoring physiological parameters of a person, in accordance with an embodiment.
Figure 8B:
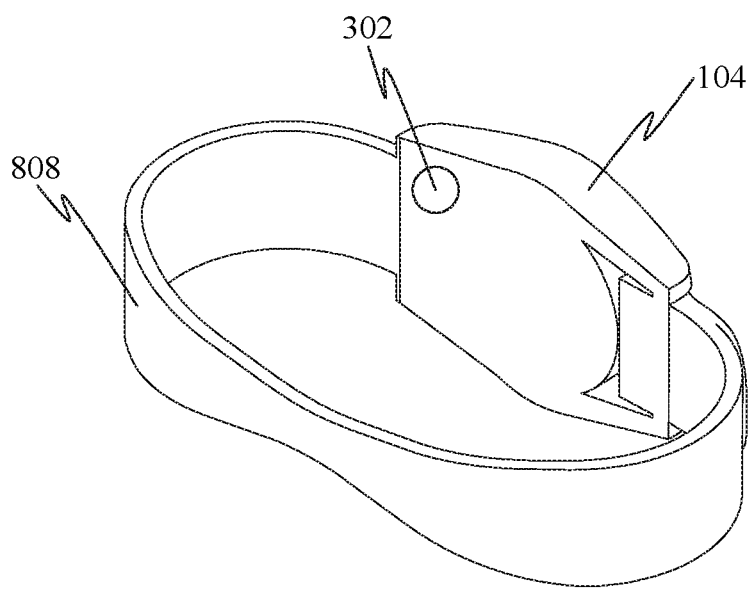
FIG. 8B is another isometric view of the medical monitoring device 104 of FIG. 8A, in accordance with an embodiment.

FIGS. 8A and 8B refers to an armband configuration of the medical monitoring device 104, in accordance with an embodiment. In the instant embodiment, the medical monitoring device 104 may further include a display 804, a power button 806, and a strap 808, among others.

The strap 808 may be configured to secure the medical monitoring device 104 to the body of the person being monitored (example: around the arm), such that, the temperature sensor 802 is in physical contact with the body. The strap 808 may be made of at least one of rubber, silicone, urethane, polyeurethane, polyvinyl chloride and any other material known in the art.

In an embodiment, the display 804 may be configured to display the physiological parameters of the person being monitored including the temperature and position of the person being monitored. The medical monitoring device 104 communicates the body temperature data and the body position data to the data processing device 106.

In an embodiment the power button 806 is configured to turn on or turn off the medical monitoring device 104.

Figure 9A:
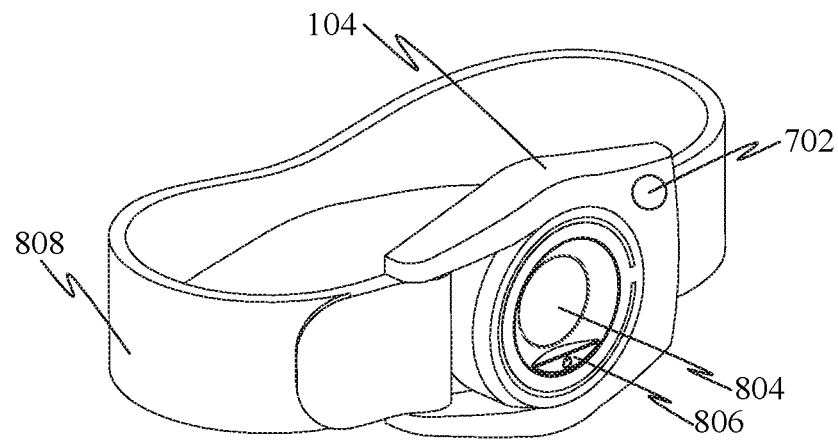
FIG. 9A is an isometric view of an armband configuration of the medical monitoring device 104 with two temperature sensors, in accordance with an embodiment.
Figure 9B:
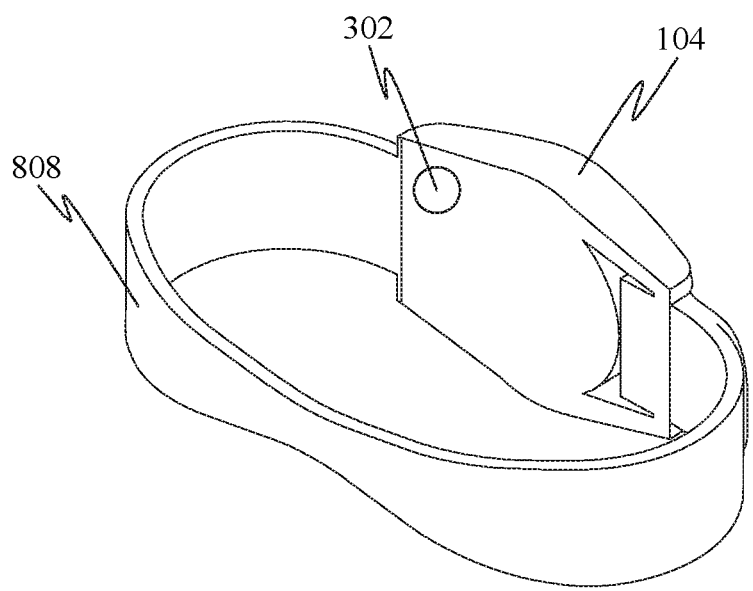
FIG. 9B is another isometric view of the medical monitoring device 104 of FIG. 9A, in accordance with an embodiment.

FIGS. 9A and 9B refers to an armband configuration of the medical monitoring device 104 with two temperature sensors, in accordance with an embodiment. The medical monitoring device 104 of FIGS. 9A and 9B is similar to the medical monitoring device 104 of FIGS. 8A and 8B with an additional second sensor 902.

Figure 10A:
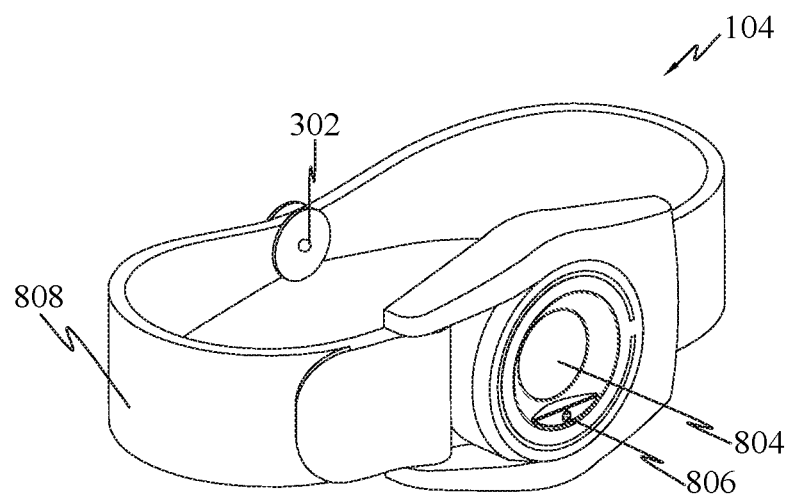
FIG. 10A is an isometric view of an armband configuration of a medical monitoring device 104 with two temperature sensors on the armband, in accordance with an embodiment.
Figure 10B:
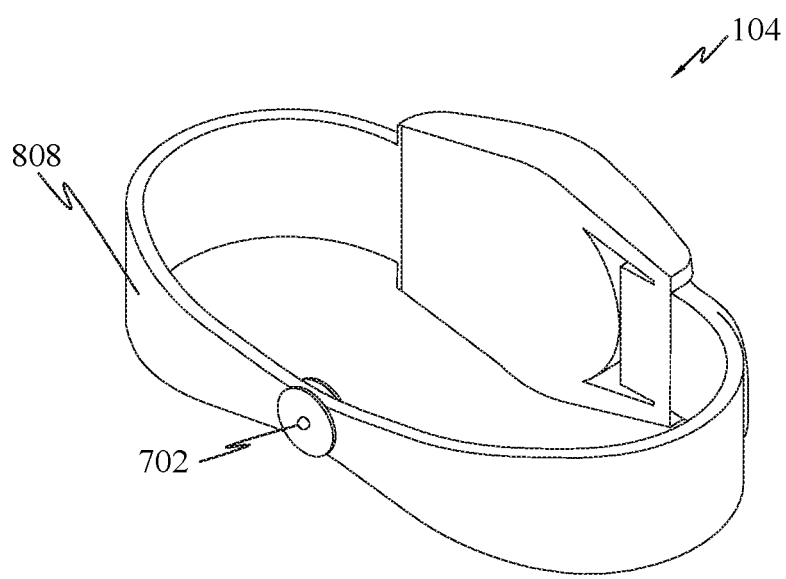
FIG. 10B is another isometric view of the medical monitoring device 104 of FIG. 10A, in accordance with an embodiment.
Figure 11A:
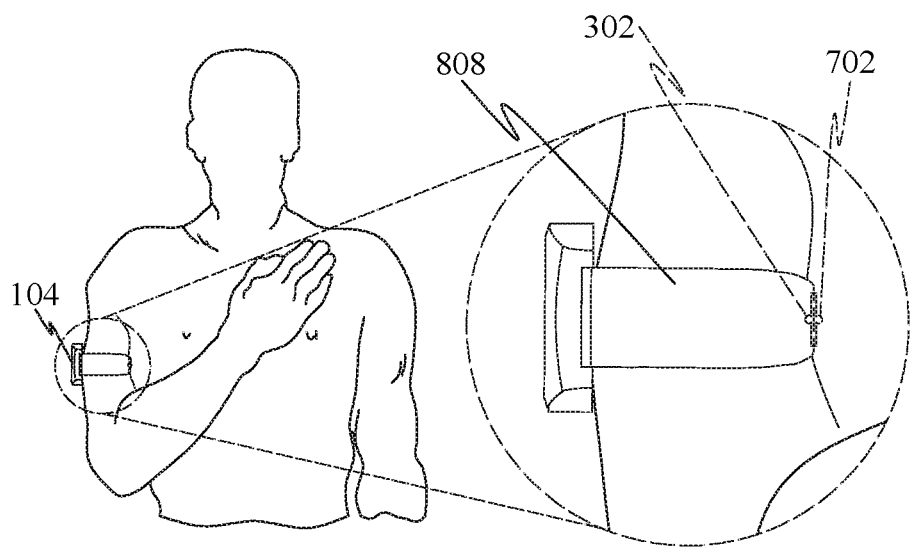
FIG. 11A illustrates the medical monitoring device 104 of FIG. 10A secured to an arm of a person, in accordance with an embodiment.
Figure 11B:
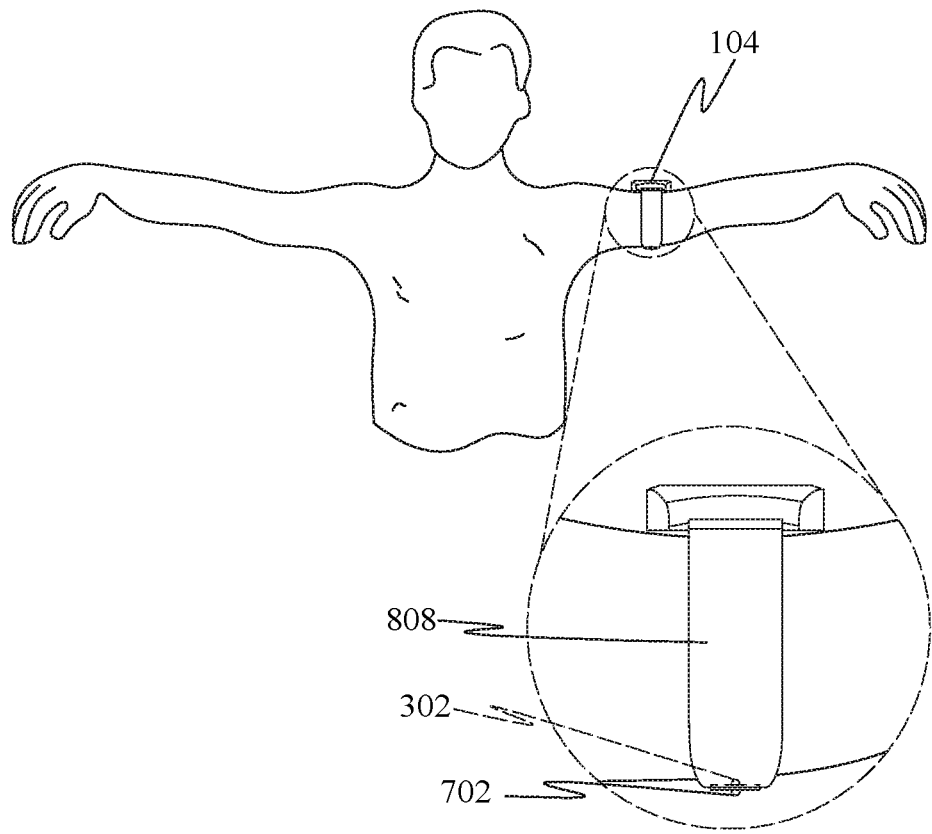
FIG. 11B illustrates the medical monitoring device 104 of FIG. 11A with the second sensor 902 positioned away from the axilla of the person, in accordance with an embodiment.

FIGS. 10A and 10B refers to an armband configuration of the medical monitoring device 104 with two temperature sensors on the armband, in accordance with an embodiment. It shall be noted that in the instant embodiment the temperature sensors (802 and 902) are positioned external (on the strap 808) to the medical monitoring device 104. In the instant embodiment, the medical monitoring device 104 may be secured to the body as shown in FIGS. 11A and 11B. The first sensor 802 and the second sensor 902 are positioned on the either sides of the strap 808 as shown in the FIGS. 10A and 10B.

In an embodiment the first sensor 802 and the second sensor 902 may be connected to the medical monitoring device 104 through the strap 808.

In an embodiment the first sensor 802 and the second sensor 902 may be wirelessly connected to the medical monitoring device 104.

FIG. 11A refers to the medical monitoring device 104 of FIG. 10A secured to an arm of a person, in accordance with an embodiment. In the instant embodiment the first sensor 802 and the second sensor 902 are insulated from ambient air as they are in contact with the body (as shown in the detailed view of FIG. 11A).

FIG. 11B illustrates the medical monitoring device 104 of FIG. 11A with the second sensor 604 positioned away from the axilla of the person, in accordance with an embodiment. In the instant embodiment the first sensor 802 and the second sensor 902 are not insulated from ambient air.

The medical monitoring device 104 may be configured to monitor physiological parameters, such as body temperature. Example of another physiological parameter that may be measured is heart rate, by using appropriate sensor(s). The disclosure provides examples of measuring body temperature. However, one skilled in the art, in light of this disclosure may make changes within the scope of the claims to measure other physiological parameters, such as heart rate. The data processing device 106 and the medical monitoring device 104 may include one or more wireless technologies that enable communication between them. The wireless technologies may be for example, BLUETOOTH, BLUETOOTH low energy, WIFI and cellular technology, among others. The use of BLUETOOTH low energy wireless technology may enable saving battery of the medical monitoring device 104 by sending information to the medical monitoring device 104 when required. The information communicated to the data processing device 106 may include the body temperature data, the ambient temperature data and the body position data of the person being monitored. The information communicated can include time stamp as well. The time stamp can include the date on which the body temperature data, the ambient temperature data and the body position data was collected.

Figure 5:
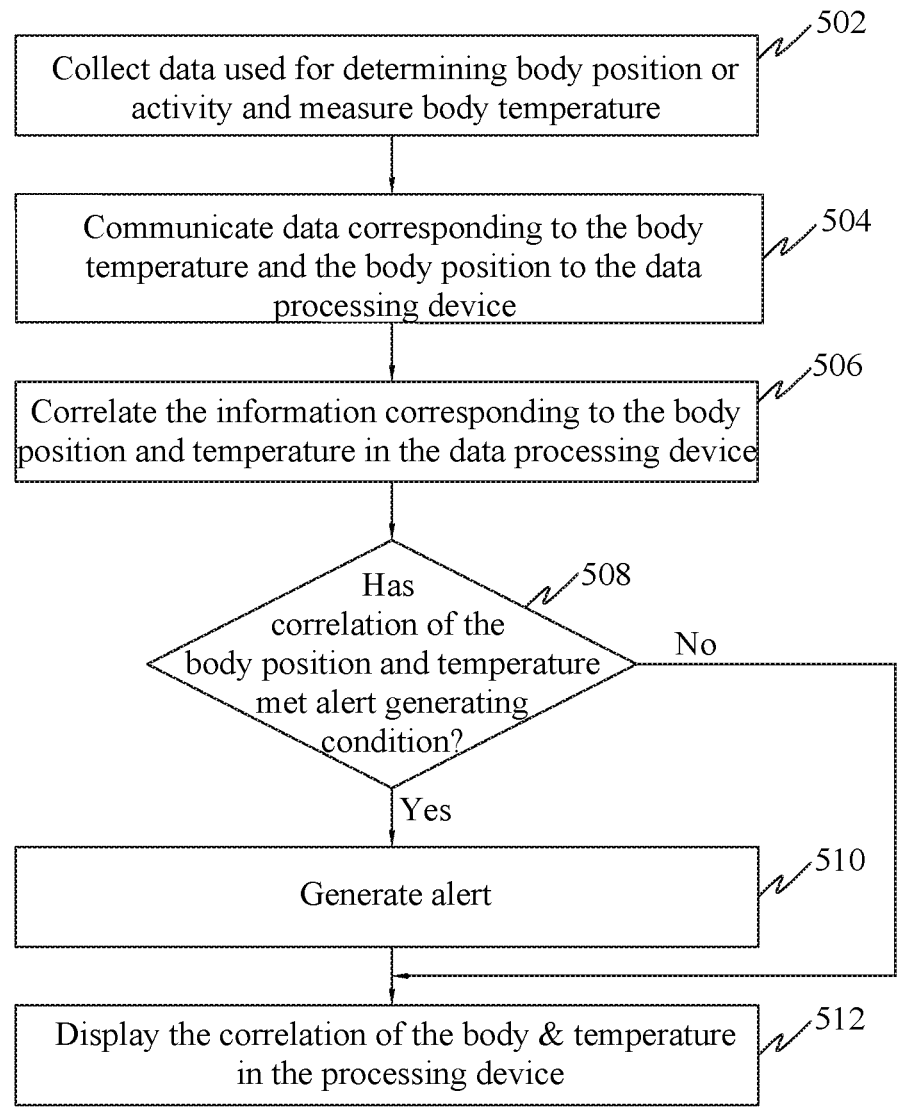
FIG. 5 is a flowchart of an exemplary method for monitoring physiological parameters of the person, in accordance with an embodiment.

Referring to FIG. 5, at step 502, the medical monitoring device 104 measures body temperature. Further, the medical monitoring device 104 collects the second data that can be used to determine the position (orientation and/or movement) of the person being monitored or the activity the person is indulged in. As an example, the position or activity can be sleeping, standing, sitting, walking and running, among others. The position or activity can be determined based on the orientation of the medical monitoring device 104 and the movements captured by the medical monitoring device 104. The data gathered by the position sensor 304 may also be used to detect any sudden/rapid movements, which may include shivering, convulsions and epileptic shocks, experienced by a person being monitored or detect that a person being monitored has fallen down.

At step 504, the medical monitoring device 104 communicates the body temperature data and the body position data to the data processing device 106. The medical monitoring device 104 may communicate a data, which may include the body temperature data and the body position data via the transmitter 306. The medical monitoring device 104 may even communicate the time and/or date at which the body temperature data and the body position data was collected. The medical monitoring device 104 may transmit the body temperature data and the body position data when data transmission condition is met. The data transmission condition may be based on one or more among time intervals, body temperature or change thereof and body position data or change thereof.

In an embodiment, the transmitter 306 may transmit data only corresponding to the body temperature.

In an embodiment, the transmitter 306 may transmit data only corresponding to the body position.

In an embodiment, the transmitter 306 may transmit data corresponding to both the body temperature and the body position.

In an embodiment, the transmitter 306 of the medical monitoring device 104 may transmit information continuously.

In an embodiment, the transmitter 306 may transmit data only when data transmission condition is met, which may be at certain intervals of time, such as, in nanoseconds, microseconds, milliseconds, seconds, minutes or hours. The time interval at which the data that may have to be sent from the medical monitoring device 104 to the data processing device 106 may be set by default or manually set.

In an embodiment, the transmitter 306 may transmit data only when the data transmission condition in the form of change in body temperature of the person is met. For example, the change of body temperature from 98° F.

In an embodiment, the transmitter 306 may transmit data only when body temperature of the person has met the data transmission condition, such as, meeting the upper or lower limit of body temperature. For example, the lower limit may be 96° F. and upper limit may be 102° F.

In an embodiment, the transmitter 306 may transmit data only when the data transmission condition in the form of change in body position of the person being monitored is met. For example, when the person being monitored changes his body position from sleeping to sitting, standing or walking.

In an embodiment, the transmitter 306 may transmit data when one or more of the time interval, body temperature and body position of the data transmission condition is met.

In an embodiment, the transmitter 306 may also transmit body position data with the body temperature data when the data transmission condition of the body temperature is met. For example, the body temperature may change and collecting and transmitting the body position data at the moment of change in body temperature may provide data, such as, the person is walking instead of sleeping, thereby resulting in change of body temperature.

In an embodiment, the transmitter 306 may also transmit the body temperature data with the body position data when the data transmission condition of the body position is met. For example, the person being monitored may experience sudden or rapid movements, which may include shivering, convulsions and epileptic shocks. Collecting and transmitting the body temperature data at this moment may provide better information about the condition of the person being monitored.

In an embodiment, the transmitter 306 may transmit information when the position sensor 304 detects sudden or rapid movements, which may include shivering, convulsions and epileptic shocks, in the person being monitored.

In an embodiment, the transmitter 306 may transmit information when the person being monitored is found to change body position/activity to shivering, walking, running, standing or sleeping, among others.

In an embodiment, the transmitter 306 may transmit information when the person being monitored is found to be falling down from the bed.

In an embodiment, the transmitter 306 may transmit information when the person being monitored is found to have fallen down from the bed.

In an embodiment, the transmitter 306 may transmit information when the temperature sensor 302 detects the body temperature is close to or equal to alert generating condition.

The data processing device 106 may be electronic devices namely personal computers, laptops, server, smart phones, tablets, cell phones and gaming consoles, among others. The data processing device 106 may include a software application configured to perform one or more activities. The one or more activities performed by the data processing device 106 include receiving the information from the transmitter 306 of the medical monitoring device 104, processing the information and displaying or enabling display of information.

At step 506, the data processing device 106 may correlate the body temperature data with the body position data of the person to present information to an end user.

The correlation of the body temperature data with the body position data of the person may be presented with respect to time. This correlation may provide an insight to a medical practitioner into the context under which the body temperature was measured. As an example, increase in body temperature of an infant combined with shivering (determined by body position data) indicates that the infant might be experiencing sudden/rapid movements, which may include convulsions and epileptic shocks.

At step 508, if the correlation of the body position data and the temperature data meets alert generating condition, then at step 510, the data processing device 106 may generate alert. The alert may be in the form of sound, light or vibration of the data processing device 106. The data processing device 106 may also generate alert in the form of sending messages or emails to cloud or other data processing device(s).

In an embodiment, the alert generating condition may be preconfigured in the data processing device 106.

In another embodiment, the alert generating condition may be manually set in the data processing device 106.

In an embodiment, the alert generation conditions may be based on one or more of the body temperature and the body position/activity data.

In an embodiment, the alert generating condition is satisfied when the body temperature of the person approaches, meets or crosses an upper or lower limit of body temperature, as predetermined.

In an embodiment, the alert generating condition is satisfied when the body temperature is not within a predetermined range.

In an embodiment, the alert generating condition is satisfied when the body position data is not within a predetermined range. The predetermined range of the body position data may refer to rate of change of one body position to another body position.

In an embodiment, the alert generating condition is satisfied when the body temperature of the person starts changing drastically, either increasing or decreasing.

In an embodiment, the alert generating conditions is satisfied when one or more of the first temperature and the second temperature are not within a predetermined range.

In an embodiment, the alert generating conditions is satisfied when the core temperature of the body is not within a predetermined range.

In an embodiment, the alert generating condition is satisfied when change in the body position/the activity of the person being monitored is determined. For example, when the person being monitored changes his body position from sleeping to sitting, standing, walking or shivering.

In an embodiment, the alert generating condition is satisfied when the position sensor 304 detects sudden or rapid movements, which may include shivering, convulsions and epileptic shocks, in the person being monitored.

In an embodiment, the alert generating condition is satisfied when the person being monitored changes body position/activity to shivering, walking, running, standing, and sleeping, among others.

In an embodiment, the alert generating condition is satisfied when the person being monitored is found to be falling down from the bed.

In an embodiment, the alert generating condition is satisfied when the person being monitored is found to have fallen down from the bed.

In an embodiment, the alert generating condition is satisfied when the temperature sensor 302 detects the body temperature is close to or equal to alert generating condition.

In an embodiment, the alert generating condition is satisfied when heart rate of the body being monitored is not within the predetermined range.

In an embodiment, the alert generating condition is satisfied when the first data is outside a predetermined range and the predetermined range is associated with each of the one or more of orientations of the body and the movements of the body.

At step 508, if the correlation of the body position and temperature has not met alert generating condition, then an alert may not be generated.

At step 512, the data processing device 106 may display the correlation of the body temperature and the body position. The correlation may be displayed in, as an example, graphical form, chart or graph, among others.

Figure 4:
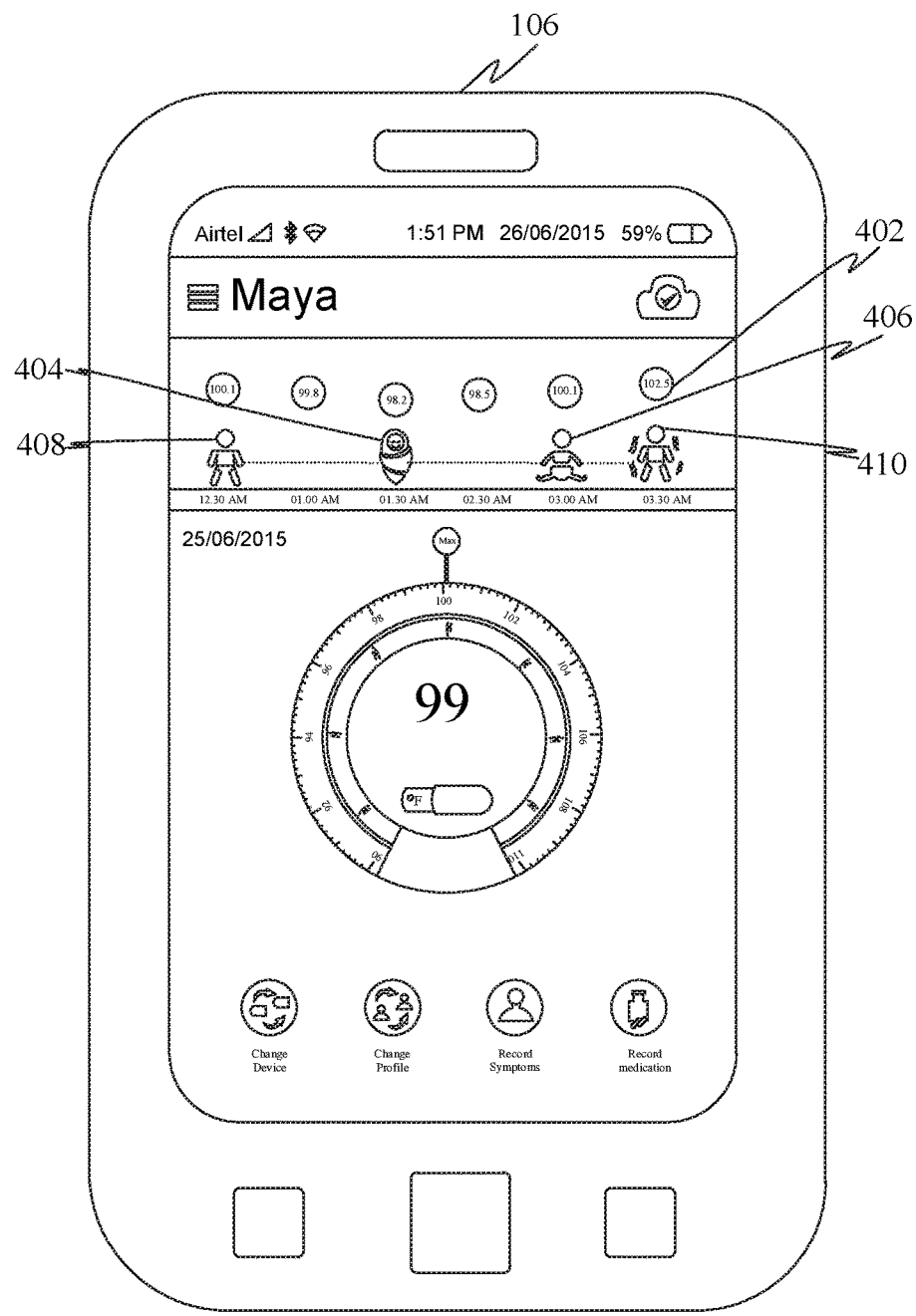
FIG. 4 illustrates an exemplary user interface of the data processing device 106 depicting the correlation between body temperature, body position/activity and time, in accordance with an embodiment.

Referring to FIG. 4, an user interface of the data processing device 106 depicts the correlation between the body temperature, body position/activity and time. The depiction indicates body temperature 402 reading against body position/activity and time. In the instant example, the body positions/activities indicated include sleeping position 404, sitting position 406, standing position 408 and experiencing sudden/rapid movements 410. Graphical representation of the position of the person being monitored or the activity of the person shown is only for representation purpose. One ordinarily skilled in the art, in light of this disclosure, may think of other body positions, body conditions or the activities of the person being monitored.

The processes described above is described as sequence of steps, this was done solely for the sake of illustration. Accordingly, it is contemplated that some steps may be added, some steps may be omitted, the order of the steps may be re-arranged, or some steps may be performed simultaneously.

Example 1: Seizure

The system 100 may enable doctors, pediatricians or anyone who is monitoring, to understand whether a patient being monitored has seizure. The medical monitoring device 104 may be attached to the external skin of a baby or infant. The medical monitoring device 104 may continuously monitor the baby. The medical monitoring device 104 may collect data indicating increasing body temperature and rapid shaking of the body. The transmitter 306 of the medical monitoring device may send the data to the data processing device 106. The data processing device 106 may combine the temperature data and the body position data to arrive at a result. The result may indicate that the person being monitored is experiencing seizure.

Example 2: Fertility Monitoring

The medical monitoring device 104 may be attached to the external skin of a woman to measure basal body temperature and determine body position of the woman while she is asleep. The medical monitoring device 104 may continuously monitor the woman during the night while she is asleep. The transmitter 306 of the monitoring device 104 may send data corresponding to the body temperature and body position to the data processing device 106. The data processing device 106 may correlate the data to arrive at a result. The result may enable one to identify the most fertile days of the woman being monitored. The result may further enable one to understand the sleep quality, the anxiety level, the stress level the woman is going through to better predict her most fertile days.

Example 3: Predict Infections in the Body

Patients who have undergone surgery and are admitted in the hospital post surgery are more susceptible to infections. Two medical monitoring devices 104 may be attached at two different locations (ex: one at axilla closer to the heart and the other at end of finger (also known as peripheral)) in the body of person being monitored. The transmitters 306 of the two medical monitoring devices 104 may transmit the temperature readings from both devices 104 to the data processing device 106. The data processing device 106 may receive the temperature readings from the two medical monitoring devices 104 and determine the difference in temperature measured at two difference locations of the body. Further, based on the difference between the two temperatures measured and body movements, the core to peripheral temperature difference of the body and the body position is determined by the data processing device 106, which may be used to indicate a number of conditions. Continuous monitoring of the person by the medical monitoring device 104 may enable prediction of sepsis in the monitored person much faster.

Embodiments provide various advantages, and one of the advantages is that a modular set-up is provided. The modular set-up enables the medical monitoring device to be used time and again, while disposing off the pouch once used, or after a few uses. Hence, the expensive portion of the setup is retained for subsequent use, thereby reducing the cost involved in monitoring.

Another advantage is that the embodiments enable determination of the context under which physiological parameter(s) (ex: body temperature) is measured. As an example, the embodiments provide data corresponding to the activity (ex: sleeping) the person was involved in, while the body temperature measurement was taken. Such context is extremely helpful in determining the health condition of a person, routine of a person and its impact on his body, among others.

Yet another advantage of the embodiments is the ability to monitor physiological parameters and providing a context under which the physiological parameters were measured, without disturbing the routine of the person being monitored.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications, these should not be construed as limiting the scope of the invention but as merely providing illustrations of some of the personally preferred embodiments of this invention.

What is claimed is:

1. A system for medical monitoring, the system comprising:
   a medical monitoring device comprising:
      a first sensor, in physical contact with a body, configured to measure a first temperature of the body at a first location on the body;
      a second sensor configured to measure a second temperature, wherein the second sensor is positioned such that the first sensor is in between the second sensor and the first location on the body;

one or more position sensors, wherein the one or more position sensors collect body position data that enable determination of one or more of an orientation of the body and movement of the body;

a processor configured to determine a core temperature of the body based on the first temperature, the second temperature and the body position data; and a pouch for operably receiving the medical monitoring device and operably taking out the medical monitoring device from the pouch, the pouch enabling the medical monitoring device to be engaged to the body, the pouch defining a first cavity receiving the medical monitoring device such that the first sensor is outside the first cavity to be in physical contact with the body, wherein the pouch defines an aperture, wherein the second sensor is exposed out of the aperture, wherein the first sensor is exposed at a first side of the pouch and the second sensor is exposed at a second side of the pouch, wherein the first side and the second side are opposite each other.

2. The medical monitoring device of claim 1, wherein the second temperature is measured, at a second location on the body, when the second sensor is in physical contact with the body.

3. The medical monitoring device of claim 1, wherein the second temperature measured by the second sensor is a temperature of ambient air surrounding the second sensor.

4. The medical monitoring device of claim 1, further comprising a display configured to display the determined core temperature of the body; and a strap configured to secure the medical monitoring device to the body.

5. The pouch of claim 1, wherein the first side of the pouch that defines the first cavity comprises adhesive to engage the pouch to the body.

6. The pouch of claim 5, wherein the adhesive is around the first cavity, leaving the first cavity adhesive free.

* * * * *